US010137037B2

(12) United States Patent
Tout et al.

(10) Patent No.: US 10,137,037 B2
(45) Date of Patent: Nov. 27, 2018

(54) REDUCED-PRESSURE, TUNNEL-WOUND DRESSINGS, SYSTEMS, AND METHODS

(71) Applicant: KCI Licensing, Inc., San Antonio, TX (US)

(72) Inventors: Aidan Marcus Tout, Alderbury (GB); Richard Daniel John Coulthard, Verwood (GB); Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 734 days.

(21) Appl. No.: 13/674,804

(22) Filed: Nov. 12, 2012

(65) Prior Publication Data

US 2013/0123723 A1 May 16, 2013

Related U.S. Application Data

(60) Provisional application No. 61/558,642, filed on Nov. 11, 2011.

(51) Int. Cl.
*A61F 13/00* (2006.01)
*A61M 1/00* (2006.01)

(52) U.S. Cl.
CPC ..... *A61F 13/00068* (2013.01); *A61M 1/0023* (2013.01); *A61M 1/0088* (2013.01); *A61F 2013/0054* (2013.01)

(58) Field of Classification Search
CPC .................. A61M 27/00; A61M 1/009; A61M 2025/0057; A61B 2017/3429; A61B 17/3431; A61F 2013/00536; A61F 2/0022
See application file for complete search history.

(56) References Cited

U.S. PATENT DOCUMENTS 1,355,846 A   10/1920   Rannells
2,547,758 A    4/1951   Keeling
(Continued)

FOREIGN PATENT DOCUMENTS

AU    550575 A1   8/1982
AU    745271      4/1999
(Continued)

OTHER PUBLICATIONS

International Search Report and Written Opinion for corresponding PCT/US2012/064689 dated Oct. 11, 2013.
(Continued)

*Primary Examiner* — Tatyana Zalukaeva
*Assistant Examiner* — Kai Weng

(57) ABSTRACT

Systems, methods, and dressing are presented for treating a tunnel wound on a patient. In one instance, a reduced-pressure, tunnel-wound dressing includes a longitudinal core member formed from a closed-cell foam that is surrounded by a first longitudinal concentric member formed from a manifolding material. When subjected to reduced pressure, the longitudinal core member expands and the first longitudinal concentric member compresses. These actions create intimate contact between the tunnel wound and the dressing, oppose collapse of the tunnel, and when reduced pressure is removed provide clearance to remove the dressing. Other embodiments are presented.

6 Claims, 8 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,708,724 B2 | 5/2010 | Weston |
| 8,771,243 B2 | 7/2014 | Khan et al. |
| 9,078,990 B1 | 7/2015 | Obst et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0131327 A1 | 6/2005 | Lockwood et al. |
| 2005/0276965 A1 | 12/2005 | Etchells |
| 2006/0041247 A1 | 2/2006 | Petrosenko et al. |
| 2008/0004657 A1* | 1/2008 | Obermiller ........ A61B 17/0057 606/213 |
| 2008/0132819 A1 | 6/2008 | Radl et al. |
| 2008/0161778 A1 | 7/2008 | Steward |
| 2009/0275884 A1* | 11/2009 | McNulty et al. ............... 604/35 |
| 2010/0036334 A1* | 2/2010 | Heagle et al. ............... 604/319 |
| 2011/0015619 A1 | 1/2011 | Svedman et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |
| WO | 2009021523 A1 | 2/2009 |

OTHER PUBLICATIONS

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University,

(56) References Cited

OTHER PUBLICATIONS

Cheboksary, U.S.S.R. 1986);pp. 94-96 (copy and certified translation.
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (copy and certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, " *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007.

* cited by examiner

REDUCED-PRESSURE, TUNNEL-WOUND DRESSINGS, SYSTEMS, AND METHODS

CROSS-REFERENCE TO RELATED APPLICATION

This application claims priority to U.S. Provisional Patent Application No. 61/558,642 filed Nov. 11, 2011, entitled REDUCED-PRESSURE, TUNNEL-WOUND DRESSINGS, SYSTEMS, AND METHODS, the disclosure of which is hereby incorporated by reference in its entirety.

BACKGROUND

1. Field

The present disclosure relates generally to medical treatment systems and, more particularly, but not by way of limitation, to reduced-pressure, tunnel-wound dressings, systems, and methods.

2. Description of Related Art

One type of wound encountered in caring for patients is a tunnel wound or sinus tract. A tunnel wound has an opening and tunnels into the patient's flesh. Tunnel wounds often involve complicated or intricate geometry. As used throughout this document, "or" does not require mutual exclusivity. A tunnel wound has a proximal opening, which may or may not be on a wound bed, and has a bottom at a distal end. A tunnel wound may extend in any direction through soft tissue underneath the skin. Tunnel wounds pose a complication risk that is due to the difficulty in removing exudate or other fluids from the tunnel wound.

Another medical issue that occurs at times is unwanted fistulas. In general terms, a "fistula" is an abnormal passage that leads from an abscess, hollow organ, or part to the body surface or from one hollow organ or part to another. The geometry and fluids involved may make treatment of fistulas difficult as well.

SUMMARY

According to an illustrative embodiment, a reduced-pressure, tunnel-wound dressing for treating a tunnel wound or a fistula includes a longitudinal core member formed from a closed-cell foam and operable to expand under reduced pressure and a first longitudinal concentric member formed from a manifold material. The first longitudinal concentric member is concentrically disposed on a circumference of the longitudinal core member. The first longitudinal concentric member is operable to compress under the reduced pressure.

According to another illustrative embodiment, a reduced-pressure system for treating a tunnel wound or fistula on a patient includes a reduced-pressure, tunnel-wound dressing. The reduced-pressure, tunnel-wound dressing includes a longitudinal core member formed from a closed-cell foam and operable to expand under reduced pressure, and a first longitudinal concentric member formed from an open-cell foam. The first longitudinal concentric member is concentrically disposed on a circumference of the longitudinal core member. The first longitudinal concentric member is operable to compress under the reduced pressure. The system also includes a drape for covering a portion of the patient's skin to form a sealed space over the reduced-pressure, tunnel-wound dressing and a reduced-pressure source fluidly coupled to the reduced-pressure, tunnel-wound dressing.

According to another illustrative embodiment, a method for treating a tunnel wound or fistula includes providing a reduced-pressure, tunnel-wound dressing. The reduced-pressure, tunnel-wound dressing includes a longitudinal core member formed from a closed-cell foam and operable to expand under reduced pressure and a first longitudinal concentric member formed from an open-cell foam. The first longitudinal concentric member is concentrically disposed on a circumference of the longitudinal core member. The first longitudinal concentric member is operable to compress under the reduced pressure. The method further includes inserting the reduced-pressure, tunnel-wound dressing into the tunnel wound or fistula and delivering reduced pressure to the reduced-pressure, tunnel-wound dressing to cause intimate contact between a tunnel margin and the reduced-pressure, tunnel-wound dressing. The longitudinal core member expands under reduced pressure and the first longitudinal concentric member compresses. The method further includes removing reduced pressure whereby the reduced-pressure, tunnel-wound dressing contracts and a gap is formed between the reduced-pressure, tunnel-wound dressing and the patient's wound margin.

According to another illustrative embodiment, a method of manufacturing a reduced-pressure, tunnel wound dressing includes extruding a longitudinal core member from a closed-cell foam, extruding a first longitudinal concentric member from an open-cell foam such that the first longitudinal concentric member is formed around the longitudinal core member, and applying a second longitudinal concentric member around the first longitudinal concentric member, wherein the second longitudinal concentric member comprises an impermeable material having a plurality of apertures.

According to another illustrative embodiment, a reduced-pressure, tunnel-wound dressing for treating a tunnel wound or a fistula includes a longitudinal core member formed from a manifold material and operable to compress under reduced pressure and a first longitudinal concentric member formed from a closed-cell foam. The first longitudinal concentric member is concentrically disposed on a circumference of the longitudinal core member. The first longitudinal concentric member is operable to expand under the reduced pressure. The reduced-pressure, tunnel-wound dressing further comprises a plurality of fluid conduits that fluidly couple the longitudinal core member and the first longitudinal concentric member.

According to another illustrative embodiment, a reduced-pressure, tunnel-wound dressing for treating a tunnel wound or a fistula includes a cylindrical, shell bladder filled with a gas. The cylindrical, shell bladder has an exterior surface, a proximal end, and a distal end. The reduced-pressure, tunnel-wound dressing further comprises an open-cell-foam layer covering the exterior surface of the cylindrical, shell bladder. The distal end of the cylindrical, shell bladder is folded back into the cylindrical, shell bladder to form a portion that is operable to unfurl when subjected to reduced pressure.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the subject matter herein, and it is understood that other embodiments may be utilized and that logical structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

The embodiments herein involve using reduced pressure to treat a tunnel wound or fistula. The dressings, methods, and systems herein may be particularly advantageous in that they allow easy placement of the dressing into the tunnel or fistula, avoid adhesion of tissue to the dressing, allow removal without retained foreign matter in the tunnel wound, or allow reduced pressure to be applied evenly on the interior surface of the tunnel or fistula. Without the systems, devices, and methods presented herein, issues may exist with tissue in-growth into the dressing, adhesions, or foreign bodies remaining in the tunnel after the dressing is removed.

Figure 1:
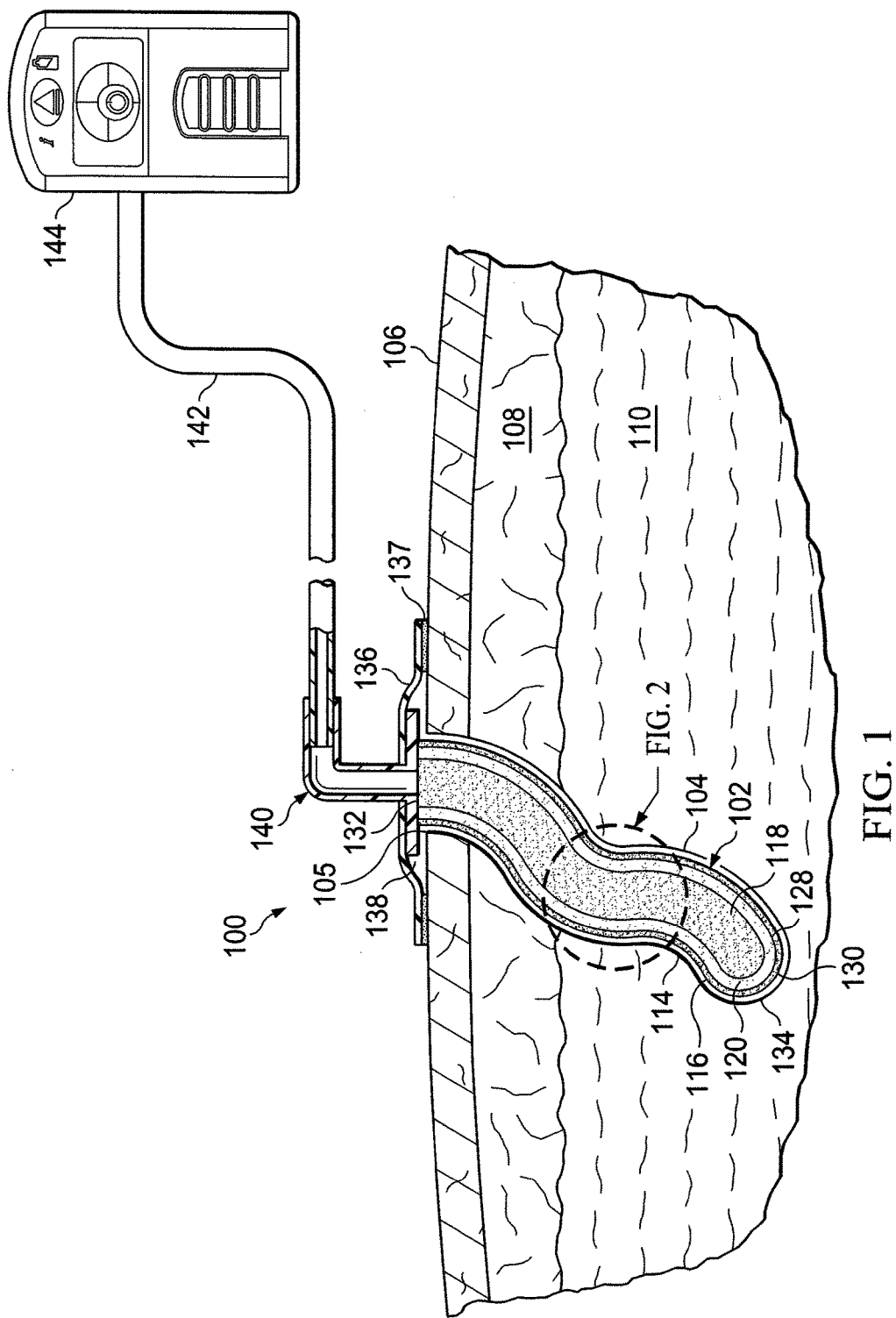
FIG. 1 is a schematic diagram with a portion shown in cross section of an illustrative embodiment of a reduced-pressure system for treating a tunnel wound (as shown) or fistula on a patient.
Figure 2:
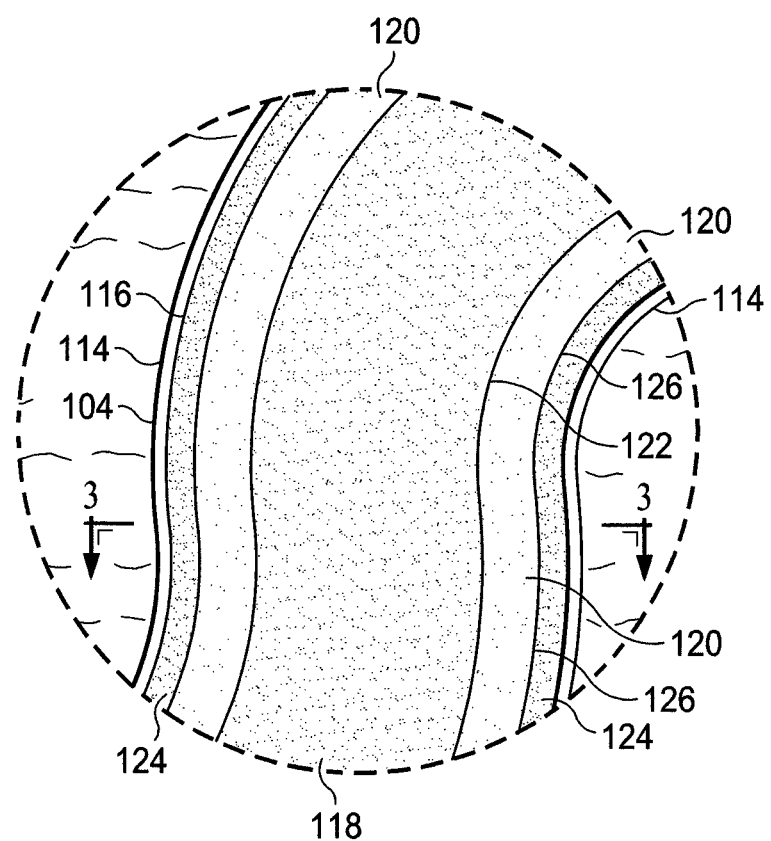
FIG. 2 is a detail of FIG. 1.
Figure 6A:
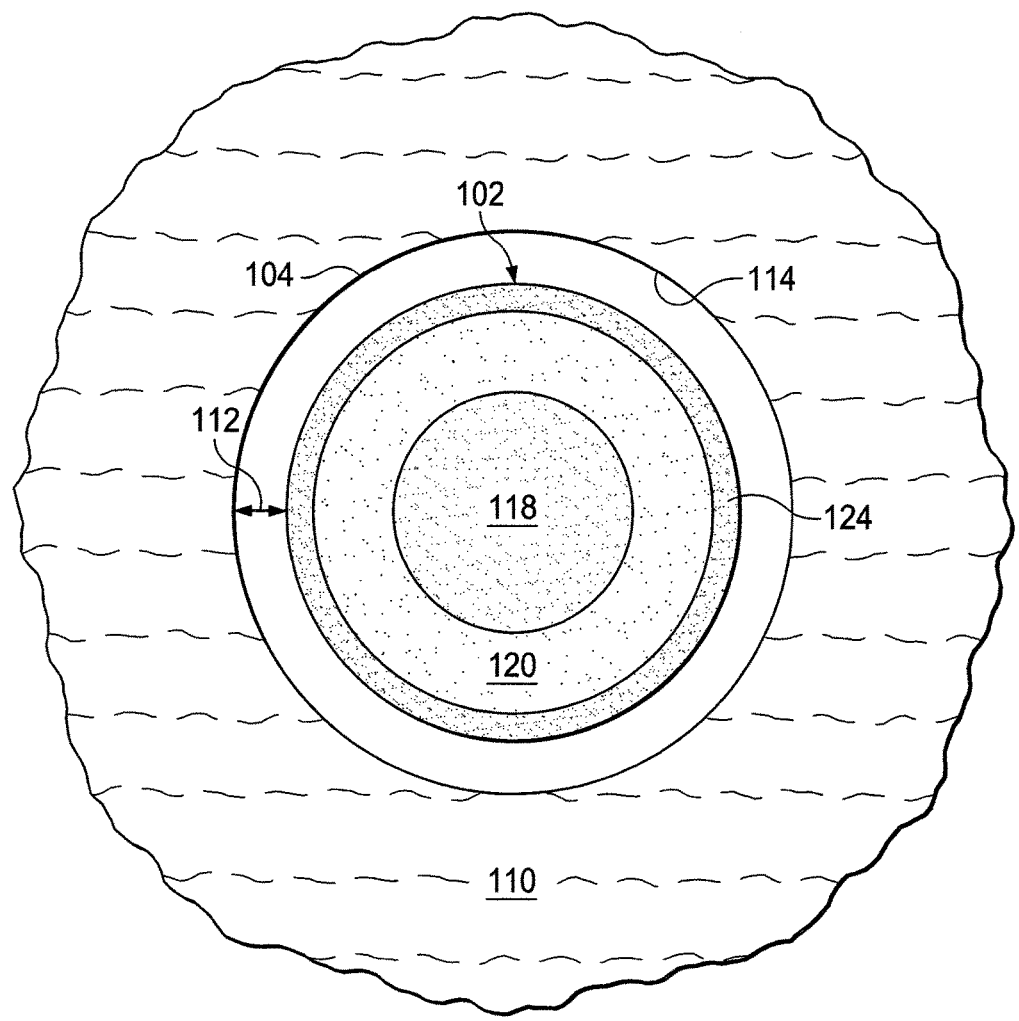
FIG. 6A is a schematic, cross section of an illustrative embodiment of a reduced-pressure, tunnel-wound dressing shown in situ before reduced pressure is applied.

Referring now primarily to FIGS. 1-4, and initially to FIG. 1, a reduced-pressure treatment system 100 having a reduced-pressure, tunnel-wound dressing 102 for treating a tunnel wound 104 or a fistula is presented. The tunnel wound 104 may have an opening 105 and extend through epidermis 106, dermis 108, and into subcutaneous tissue 110 as shown, or may extend from a wound bed. The reduced-pressure, tunnel-wound dressing 102 is stiff enough to allow insertion into the tunnel wound 104 and yet flexible enough to conform to the path of the tunnel wound 104. This is important when tunnel wounds extend deeper than 10 centimeters as they frequently do. The reduced-pressure, tunnel-wound dressing 102 is sized to have a smaller diameter than the tunnel wound 104 so that a gap 112 (FIG. 6A) exists between a tunnel-wound margin 114 and the reduced-pressure, tunnel-wound dressing 102. When reduced pressure is applied to the reduced-pressure, tunnel-wound dressing 102, the tunnel-wound margin 114 comes into intimate contact with an exterior surface 116 of the reduced-pressure, tunnel-wound dressing 102. The intimate contact is due to the reduced-pressure, tunnel-wound dressing 102 expanding under the influence of reduced pressure, or the reduced pressure pulling the tunnel-wound margin 114 to the reduced-pressure, tunnel-wound dressing 102 as will be explained below.

The reduced-pressure, tunnel-wound dressing 102 includes a longitudinal core member 118 formed from a closed-cell foam and operable to expand under reduced pressure. The reduced-pressure, tunnel-wound dressing 102 also includes a first longitudinal concentric member 120 formed from an open-cell foam or other manifolding material. The first longitudinal concentric member 120 is concentrically disposed on a circumference 122 or exterior surface on a longitudinal portion of the longitudinal core member 118. The first longitudinal concentric member 120 is operable to compress under the reduced pressure and to transmit fluids. The reduced-pressure, tunnel-wound dressing 102 may also include a second longitudinal concentric member 124 formed from a non-adherent material having a plurality of apertures, which may be pores or larger openings. The second longitudinal concentric member 124 is concentrically disposed on a circumference 126 of the first longitudinal concentric member 120 and further covers a distal end 128 of the first longitudinal concentric member 120. These components will be further described below.

The longitudinal core member 118 is formed from a closed-cell foam that provides rigidity to aid in placement of the reduced-pressure, tunnel-wound dressing 102. The longitudinal core member 118 is stiff enough to facilitate insertion into the tunnel wound 104—even deep tunnel wounds—and yet flexible enough to follow the path of the tunnel wound 104 even when the tunnel wound 104 includes curves or turns. The longitudinal core member 118 expands under reduced pressure. In other words, the longitudinal core member 118 has an effective lateral diameter of $D_A$ without reduced pressure but, when reduced pressure is applied around the longitudinal core member 118, captured gas in the closed cells causes the longitudinal core member 118 to expand to have a diameter $D_B$, where $D_B > D_A$. This expansion forms or helps form intimate contact between the exterior surface 116 of the reduced-pressure, tunnel-wound dressing 102 and the tunnel margin 114. In one embodiment, the longitudinal core member 118 may expand under reduced pressure greater than a first threshold reduced pressure. The first threshold reduced pressure may be determined by the material properties of the closed-cell foam forming the longitudinal core member 118, e.g., the elastic properties, and/or the composition of the gas held within the closed-cell foam. The longitudinal core member 118 is the inner most portion of the reduced-pressure, tunnel-wound dressing 102. The longitudinal core member may be formed from elastic foamed materials such as polyurethane, thermoplastic elastomers, polyethylene vinyl acetate (EVA), polyisoprene, polystyrene butadiene, polyisobutylene, fluoropolymers, silicone elastomers or other materials.

The first longitudinal concentric member 120 is disposed outboard of the longitudinal core member 118. The first longitudinal concentric member 120 is formed from a porous, open-cell foam or other material that is operable to transmit reduced pressure and fluids. In other words, the first longitudinal concentric member 120 functions as a manifold. The first longitudinal concentric member 120 may be formed from GRANUFOAM foam available from KCI Inc. of San Antonio, Tex.; a polyvinyl alcohol foam, e.g., a WHITE FOAM which is also available from KCI Inc.; a polyurethane foam; polyvinyl alcohol foam; an open-cell polyolefin foam; thermoplastic elastomers, polyethylene vinyl acetate (EVA), polyisoprene, polystyrene butadiene, polyisobutylene, fluoropolymers, silicone elastomers, or other similar material, for example. The foam may be plasticized to help maintain flexibility.

The second longitudinal concentric member 124 is the most outboard member of the reduced-pressure, tunnel-wound dressing 102. The second longitudinal concentric member 124 is a member that inhibits in-growth of tissue. The second longitudinal concentric member 124 may be lubricious to ease placement of the reduced-pressure, tunnel-wound dressing 102 in the tunnel wound 104. The second longitudinal concentric member 124 may be a hydrophilic, slippery member; micro-porous filter membrane member, e.g., a PTFE member, a GORE material; perforated polyurethane film; a sintered polymer with apertures; hydrophilic micro-porous or micro-perforated silicone elastomer, microporous or micro-perforated polyester or acrylic membranes coated or plasma treated to confer hydrophilic characteristics. Apertures (not explicitly shown) in the second longitudinal concentric member 124 may be 10 to 20 micron pores or may be larger apertures.

The second longitudinal concentric member 124 may have marking along the longitudinal length to help gauge depth of the tunnel wound 104. The color or texture of the second longitudinal concentric member 124 may also be used to help identify any missing portions upon removal from the tunnel wound 104. In this regard, it should be noted that the longitudinal core member 118, first longitudinal concentric member 120, or second longitudinal concentric member 124 may be formed with a radiopaque marker applied to help locate or identify any portions of the reduced-pressure, tunnel-wound dressing 102 that may be retained within the tunnel wound 104.

Figure 3A:
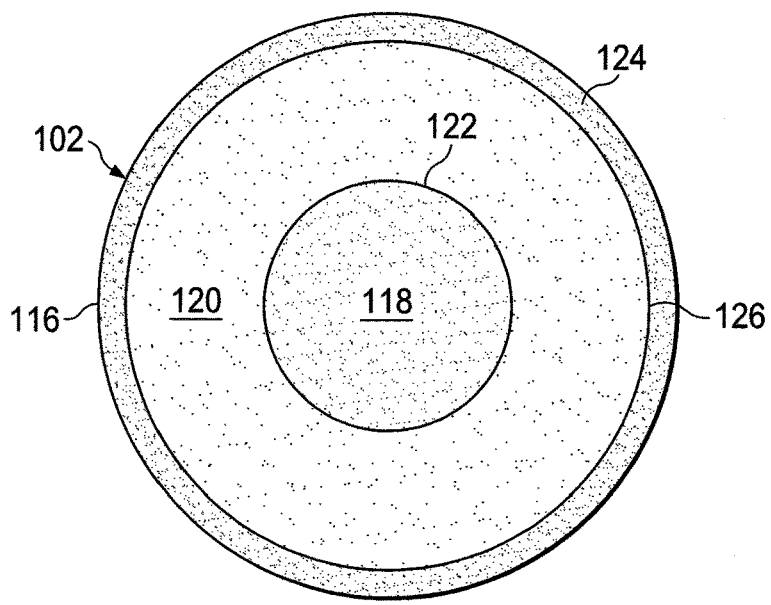
FIG. 3A is a lateral cross section of the reduced-pressure, tunnel-wound dressing of FIGS. 1-2 shown without reduced pressure applied.
Figure 3B:
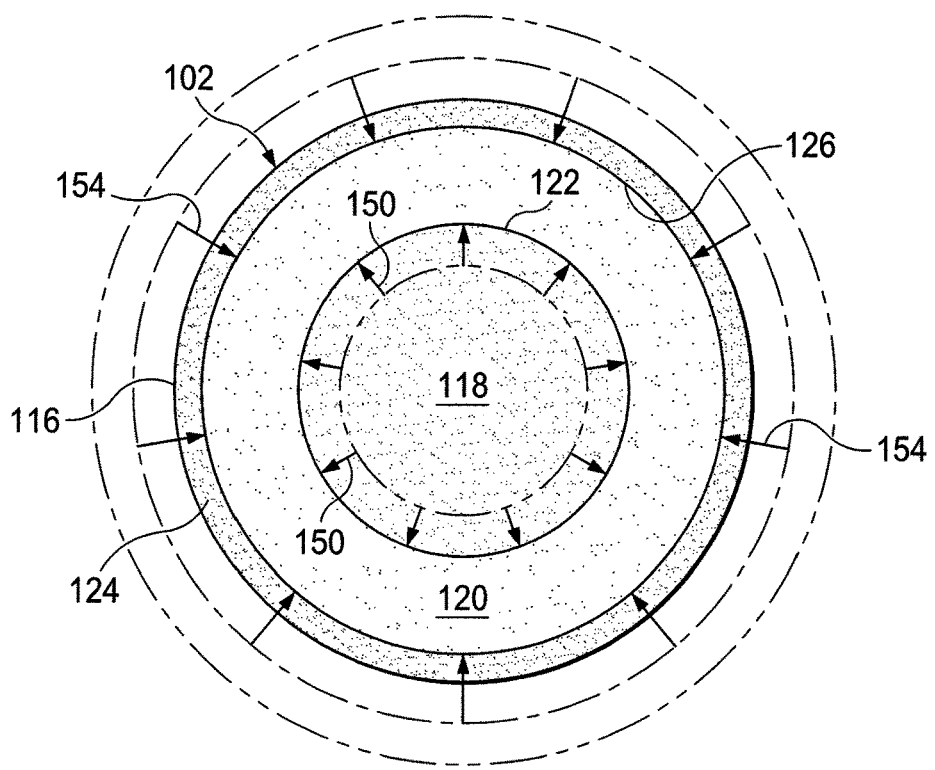
FIG. 3B is the reduced-pressure, tunnel-wound dressing of FIG. 3A with reduced pressure applied and arrows showing relative movements.
Figure 5:
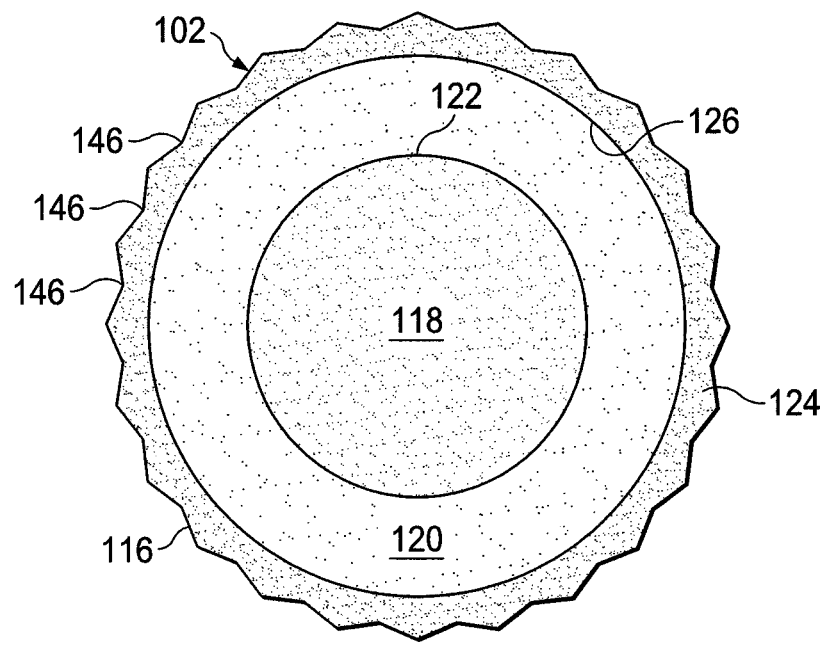
FIG. 5 is a schematic, lateral cross section of an illustrative embodiment of a reduced-pressure, tunnel-wound dressing similar to FIG. 3A, but shown with a faceted second longitudinal concentric member.

The second longitudinal concentric member 124 and the first longitudinal concentric member 120 may form a smooth rounded surface as shown in FIG. 3A or may form a surface with a plurality of facets 146 as shown in FIG. 5. The plurality of facets 146 help distribute the reduced pressure at the tunnel margins. The plurality of facets 146 help provide fluid movement particularly during the initial phases of applying reduced pressure and help assure that fluids are communicated to the distal end 130. Fluids are drawn into the area proximate the facets 146.

The reduced-pressure, tunnel-wound dressing 102 has a distal end 130 and a proximal end 132. The distal end 130 may be positioned proximate to a bottom 134 of the tunnel wound 104. The proximal end 132 may be flush with the epidermis 106 (or wound bed) or may extend beyond the epidermis 106 (or wound bed). A sealing member 136 is placed over the proximal end 132 to form a sealed space 138. The proximal end 132 is in the sealed space 138. The sealing member 136 may be any material that provides a fluid seal. A fluid seal is adequate to maintain reduced pressure at a desired site given the particular reduced-pressure source or subsystem involved. The sealing member 136 may be, for example, an impermeable or semi-permeable, elastomeric material. For semi-permeable materials, the permeability must be low enough that for a given reduced-pressure source, the desired reduced pressure may be maintained. If the tunnel wound 104 extends from a wound bed, a manifold member may be placed over the wound bed and the proximal end 132 before covering with the sealing member 136. Thus, the manifold member and proximal end 132 are in the sealed space 138.

The sealing member 136 includes an attachment device 137 on a patient-facing side. The attachment device 137 may be a medically acceptable, pressure-sensitive adhesive that extends about a periphery, a portion, or the entire sealing member 136; a double-sided drape tape; paste; hydrocolloid; hydrogel; or other sealing devices or elements.

The term manifold generally refers to a substance or structure that is provided to assist in applying reduced pressure to, delivering fluids to, or removing fluids from the wound bed. The manifold typically includes a plurality of flow channels or pathways that distribute fluids provided to and removed from the wound bed around the manifold. In one illustrative embodiment, the flow channels or pathways are interconnected to improve distribution of fluids provided to or removed from the wound bed. Examples of manifolds include, without limitation, devices that have structural elements arranged to form flow channels, such as, for example, cellular foam, open-cell foam, porous tissue collections, liquids, gels, and foams that include, or cure to include, flow channels; foam, gauze, felted mat, or any other material suited to a particular biological application; a porous foam that may include a plurality of interconnected cells or pores that act as flow channels, e.g., a polyurethane, open-cell, reticulated foam such as GranuFoam® material manufactured by Kinetic Concepts, Incorporated of San Antonio, Tex. In some situations, the manifold may also be used to distribute fluids such as medications, antibacterials, growth factors, and various solutions to the tissue site Other layers may be included in or on the manifold, such as absorptive materials, wicking materials, hydrophobic materials, and hydrophilic materials.

A reduced-pressure interface 140 may be used to fluidly couple a reduced-pressure conduit 142 to the sealed space 138. In one illustrative embodiment, the reduced-pressure interface 140 is a T.R.A.C.® Pad or Sensa T.R.A.C.® Pad available from KCI of San Antonio, Tex. Alternatively, the reduced-pressure conduit 142 may be inserted through the sealing member 136 into the sealed space 138.

The reduced-pressure conduit 142 is also fluidly coupled to a reduced-pressure source 144. The reduced-pressure source 144 provides reduced pressure. The reduced-pressure source 144 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg (−667 Pa) and −500 mm Hg (−66.7 kPa), more typically between −75 mm Hg (−9.9 kPa) and −300 mm Hg (−39.9 kPa), and more typically still between −25 mm (−3.33 kPa) and −200 mm Hg (26.6 kPa).

The amount of reduced pressure may be used to control the force between the exterior surface 116 of the reduced-pressure, tunnel-wound dressing 102 and the tunnel margin 114.

Reduced pressure refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently.

Referring primarily to FIG. 3A, the relative areas and dimensions of the components shown in lateral cross section may be varied. The whole diameter of the reduced-pressure, tunnel-wound dressing 102 may vary according to common sizes of the tunnel wound 104, e.g., 0.25 centimeters to 8 centimeters in length. Depending on the overall desired size, the second longitudinal concentric member 124 may range from 0 to 20 microns in thickness and is typically in the 10-15 micron range. The first longitudinal concentric member 120 may range from 2 mm to 4 cm in thickness. The longitudinal core member 118 may have a diameter that ranges from 1 cm to 5 cm. These dimensions are set forth as examples and are not intended to be limiting. The reduced-pressure, tunnel-wound dressing 102 may be varied as desired to accommodate differently sized tunnel wounds. In terms of relative areas on a lateral cross section, the longitudinal core member 118 will typically be in the range of 20% to 90%. The first longitudinal concentric member 120 will typically be in the range of 10% to 60%. The second longitudinal concentric member 124 may vary from 0% to 10% and more typically between 0% and 2%.

Figure 4:
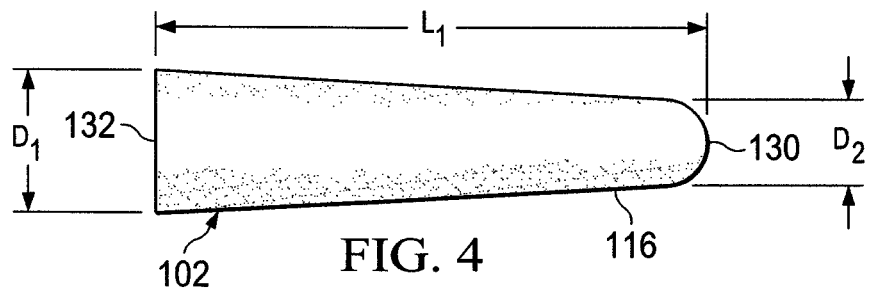
FIG. 4 is a schematic, longitudinal side view of the illustrative embodiment of a reduced-pressure, tunnel-wound dressing of FIG. 1.

As shown in FIG. 4, the reduced-pressure, tunnel-wound dressing 102 may be tapered in its longitudinal profile between the proximal end 132 and the distal end 130 or any portion thereof. The larger diameter is usually the proximal end 132. For example the proximal end 132 may have an effective cross sectional diameter $D_1$ and the distal end 130 (or actually near the distal end 130 but in-board a small distance, e.g. 5% of the longitudinal length $L_1$) may have an effective cross sectional diameter of $D_2$, wherein $D_1$ is greater than $D_2$. Since healing occurs from the bottom outward, the taper may assist with this pattern of healing. In some embodiments, the reduced-pressure, tunnel-wound dressing 102 may not be tapered but may have a constant profile in its longitudinal side view.

In some embodiments, the second longitudinal concentric member 124 may be omitted. In such a case, the first longitudinal concentric member 120 may be formed from an open cell foam having a pore size of at least 160 pore per inch (ppi) to inhibit tissue in-growth. Moreover, using the higher density foam without a second longitudinal concentric member 124 will facilitate cutting the distal end 130 without an issue of in-growth.

Referring to FIGS. 1-4 and 6A-6B, in operation, according to one illustrative embodiment, the reduced-pressure, tunnel-wound dressing 102 is sized as an initial step. Sizing the reduced-pressure, tunnel-wound dressing 102 may entail selecting a dressing with an effective diameter at the widest that is smaller than the diameter of the tunnel wound 104. In other words, the reduced-pressure, tunnel-wound dressing 102 is selected so that the gap 112 (FIG. 6A) exists between the exterior surface 116 and the tunnel margin 114. Sizing may also include selecting an appropriate length reduced-pressure, tunnel-wound dressing 102 so that the distal end 130 is at or near the bottom 134 and the proximal end 132 is flush with the epidermis 106 or wound bed or extends beyond only a small way, e.g., 5 to 10% of the length of the reduced-pressure, tunnel-wound dressing 102. The length may also be adjusted by cutting the proximal end 132 or, in some cases, the distal end 130. If the distal end 130 is cut, the distal end 130 may need to be covered with a perforated sealing material.

The sized reduced-pressure, tunnel-wound dressing 102 is inserted into the tunnel wound 104 until the distal end 130 is proximate to the bottom 134 of the tunnel wound 104. If a fistula is being treated, the reduced-pressure, tunnel-wound dressing 102 is inserted a distance estimated to fill the fistula. If the opening 105 of the tunnel-wound 104 is on a wound bed, a manifold member may be placed over the wound bed and the proximal end 132 of the reduced-pressure, tunnel-wound dressing 102.

The reduced-pressure, tunnel-wound dressing 102 and the manifold member, if applicable, are covered by the sealing member 136 to create the sealed space 138. The sealing member 136 is held against the intact epidermis 106 by the attachment device 137.

The reduced-pressure conduit 142 is fluidly coupled to the sealed space 138. This may be accomplished by applying the reduced-pressure interface 140 under the sealing member 136 and coupling the reduced-pressure conduit 142 thereto. Alternatively, an aperture may be formed in the sealing member 136 and an end of the reduced-pressure conduit 142 inserted through the aperture and sealed. Once fluidly coupled, reduced pressure is delivered through the reduced-pressure conduit 142 to the sealed space 138.

Figure 6B:
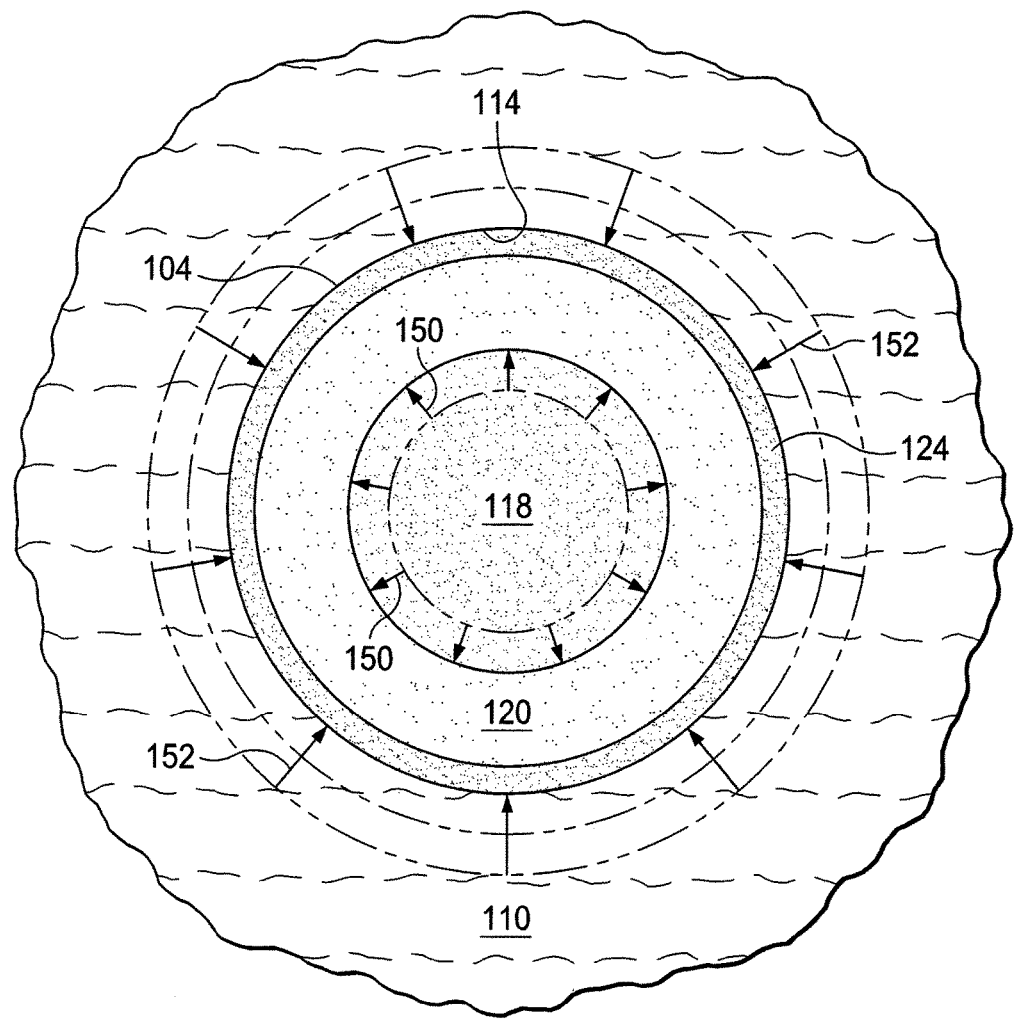
FIG. 6B is the reduced-pressure, tunnel-wound dressing of FIG. 6A shown with reduced pressure applied.

Referring now to FIGS. 3A-3B and 6A-6B, the effect of the reduced pressure will be explained. Before the reduced pressure is applied (FIGS. 3A and 6A), the reduced-pressure, tunnel-wound dressing 102 has a diameter $D_a$ and fits in the tunnel wound 104 with a gap 112 between the tunnel margin 114 and the exterior surface 116 of the reduced-pressure, tunnel-wound dressing 102. Once the reduced pressure is applied (FIGS. 3B and 6B), the longitudinal core member 118 expands as suggested by arrows 150—the expansion is due to the expansion of the gas in the closed cells as the ambient pressure is reduced on an absolute pressure scale. The reduced pressure also urges the tunnel margin 114 towards the reduced-pressure, tunnel-wound dressing 102 as suggested by arrows 152 (FIG. 6B). In addition, the first longitudinal concentric member 120 compresses as suggested by arrows 154 (FIG. 38). One or more of these movements causes intimate contact between the reduced-pressure, tunnel-wound dressing 102 and the tunnel margin 114. The reduced pressure is applied for as long as treatment is desired. After the desired treatment time, reduced pressure is removed. It may be desirable to remove the reduced pressure in stages to avoid trauma to the tunnel wound 104.

As a result of removing the reduced pressure, the longitudinal core member 118 contracts to its original size or approximately its original size and the first longitudinal concentric member 120 expands to its original size or approximately its original size. In addition, the gap 112 or a portion of the gap 112 between the tunnel margin and the reduced-pressure, tunnel-wound dressing 102 is restored. One or more of these changes facilitates a withdrawal of the reduced-pressure, tunnel-wound dressing 102 from the tunnel wound 104. In some embodiments, saline or another liquid may be transmitted under positive pressure into the reduced-pressure, tunnel-wound dressing 102 to facilitate removal of the reduced-pressure, tunnel-wound dressing 102 from the tunnel wound 104. Also, fluids may be introduced during treatment as discussed in connection with the embodiment of FIG. 8.

The reduced-pressure, tunnel-wound dressing 102 may be manufactured using many techniques. According to one illustrative embodiment, the components or a sum of them are co-extruded. The longitudinal core member 118 may be extruded as a closed cell foam and then open cell foam may be extruded around the longitudinal core member 118 to form the first longitudinal concentric member 120. The second longitudinal concentric member 124 may be applied to the circumference 126 of the first longitudinal concentric member 120. If the second longitudinal concentric member 124 is not porous enough, a pin may be used to perforate the second longitudinal concentric member 124 or a laser may be used to create apertures. If the laser is used, it may have limited power application or it may be applied at a tangent to avoid penetrating the longitudinal core member 118. Alternatively, the longitudinal core member 118 may be extruded and then coated with the material that forms the first longitudinal concentric member 120. Alternatively, styrene beads filled with gas may be heated to form the longitudinal core member 118 and then open cell foam extruded over the longitudinal core member 118 to form the first longitudinal concentric member 120.

The second longitudinal concentric member 124 may be formed by a lapping material or formed with a wind angle. A hot melt could be used to fuse the portions. The second longitudinal concentric member 124 may also be extruded on the outside of the first longitudinal concentric member 120.

Figure 7:
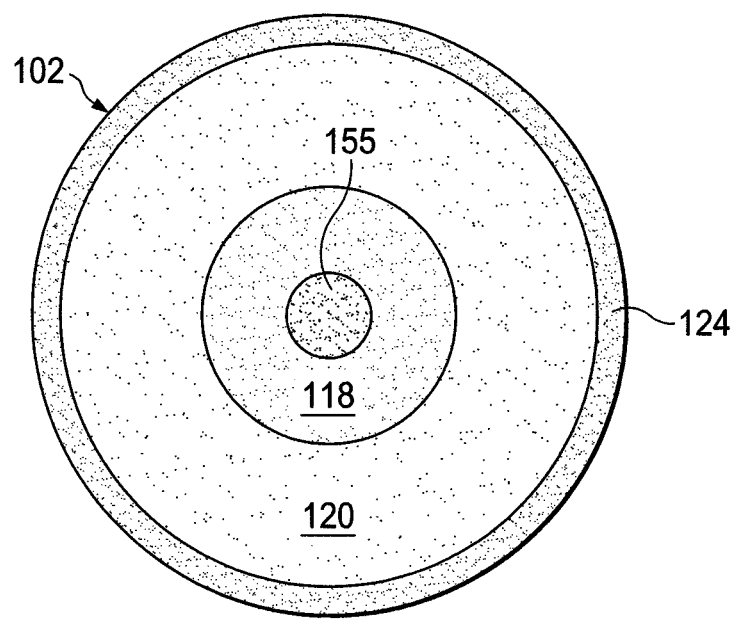
FIG. 7 is a schematic, lateral cross section of a reduced-pressure, tunnel-wound dressing that includes a semi-rigid inner-core member.

Referring now primarily to FIG. 7, the reduced-pressure, tunnel-wound dressing 102 is shown in a lateral cross section with a semi-rigid, inner-core member 155. The addition of this semi-rigid, inner-core member 155 adds rigidity to the reduced-pressure, tunnel-wound dressing 102. The additional rigidity may further assist in placing the reduced-pressure, tunnel-wound dressing 102 in intricate tunnel wounds 104. The semi-rigid, inner-core member 155 may be formed from conformable silicone, polyurethanes, thermoplastic elastomers, crosslinked elastomers, or other similar materials, for example.

Figure 8:
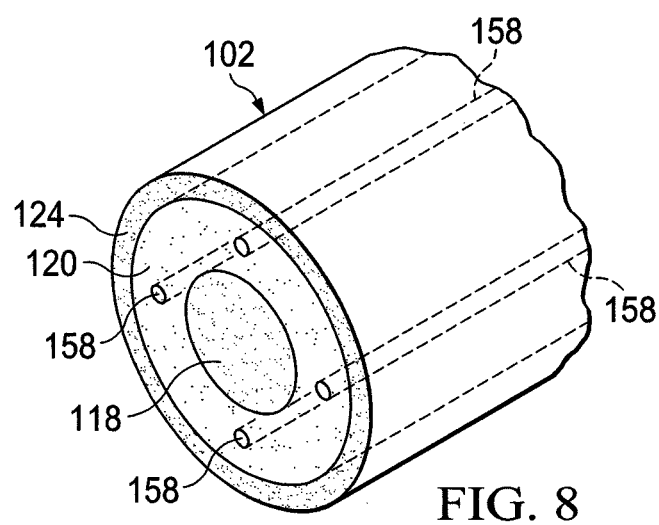
FIG. 8 is a schematic, perspective view, with a portion shown in cross section, of another illustrative embodiment of a reduced-pressure, tunnel-wound dressing having a plurality of liquid conduits.

Referring now to FIG. 8, the reduced-pressure, tunnel-wound dressing 102 is shown with a plurality of liquid conduits 158 added. The liquid conduits 158 may be used to provide medicaments such as flushing liquids to the tunnel wound 104. While not explicitly shown, the liquid conduits 158 may have a plurality of apertures along its longitudinal length to distribute the liquids throughout the tunnel wound 104.

Figure 9:
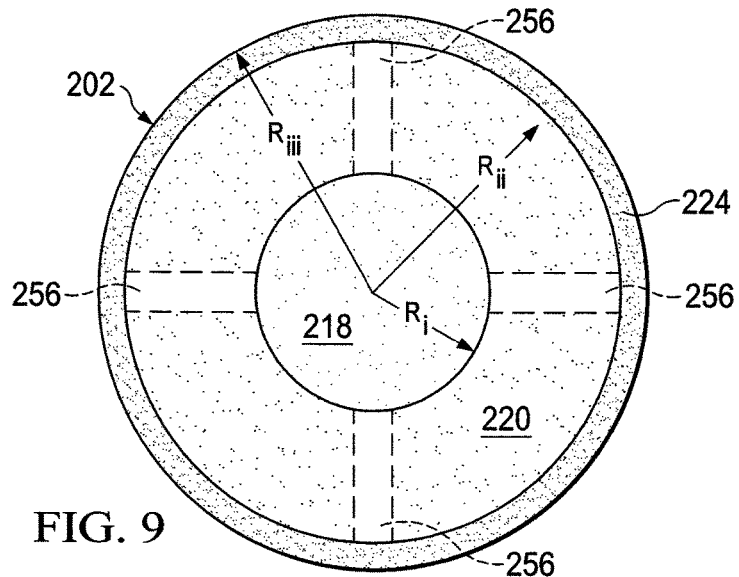
FIG. 9 is a schematic, lateral cross section of a reduced-pressure, tunnel-wound dressing showing an alternative embodiment.

Referring now primarily to FIG. 9, another embodiment of a reduced-pressure, tunnel-wound dressing 202 is presented. The reduced-pressure, tunnel-wound dressing 202 has a longitudinal core member 218 formed from an open cell foam and having a lateral outside radius $R_i$. A first longitudinal concentric member 220 surrounds the longitudinal core member 218 and has a lateral outside radius $R_{ii}$. A second longitudinal concentric member 224 may surround the first longitudinal concentric member 220. The second longitudinal concentric member 224 has a lateral outside radius $R_{iii}$ The longitudinal core member 218 in this embodiment is made from similar materials and has similar dimensions and functionality as the first longitudinal concentric member 120 in FIG. 1. The first longitudinal concentric member 220 is made from similar materials and has similar dimensions and functionality as the longitudinal core member 118 of FIG. 1. A plurality of conduits 256 fluidly couple the second longitudinal concentric member to the longitudinal core member 218, which in this embodiment function as the manifold. With the reduced-pressure, tunnel-wound dressing 202, it may be advantageous to use a faceted second longitudinal concentric member 224 such as the one shown in FIG. 5. The facets help distribute reduced pressure to the tunnel margins.

The longitudinal core member 218 transmits the reduced pressure down the center of the reduced-pressure, tunnel-wound dressing 202 to the conduits 256 or to an end opening (not shown). The reduced pressure is minimally restricted in this way as is travels along the longitudinal core member 218. As such, a more significant pressure differential may be achieved at the distal end. Transmission of reduced pressure with the reduced-pressure, tunnel-wound dressing 202 in this way may drive the closure of the tunnel wound 104 (FIG. 1) from the bottom 134 by drawing the reduced-pressure, tunnel-wound dressing 202 back from the farthest reach or section of the tunnel wound. This, in turn, will contract the bottom 104 of the tunnel wound 104 and aid in promoting the adhesion of one side of the tunnel wall to the other in the form of tertiary closure. The presence of the reduced-pressure, tunnel-wound dressing 202 may delay primary closure until the wound has been closed from the bottom up.

Figure 10A:
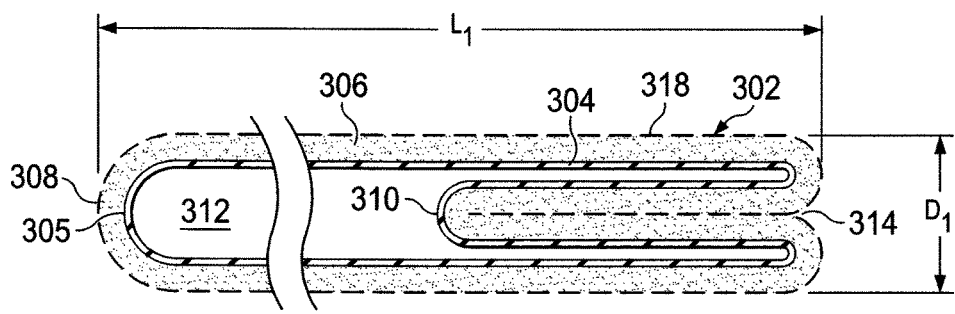
FIG. 10A is a schematic, longitudinal cross section of another illustrative embodiment of a reduced-pressure, tunnel-wound dressing having a cylindrical, shell bladder filled with a gas and shown without reduced pressure applied.
Figure 10B:
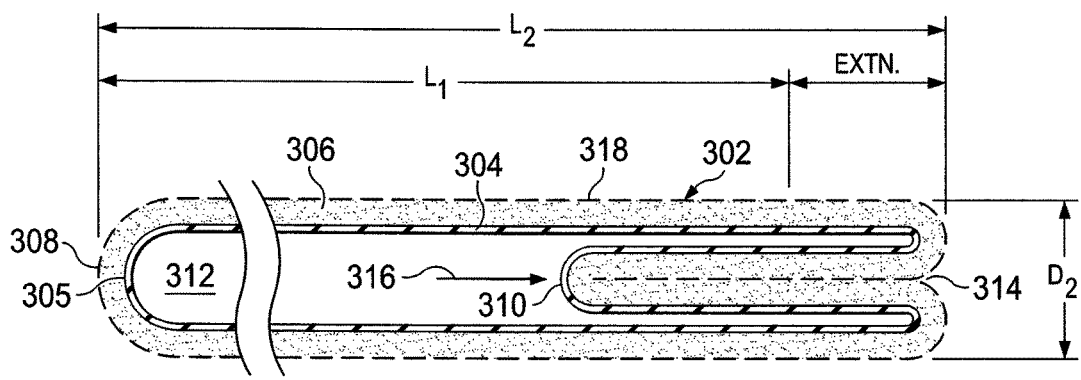
FIG. 10B is a schematic, longitudinal cross section of the illustrative embodiment of a reduced-pressure, tunnel-wound dressing of FIG. 10A shown with reduced pressure applied.

Referring now to FIGS. 10A and 10B, an alternative reduced-pressure, tunnel-wound dressing 302 is presented. In this embodiment, the reduced-pressure, tunnel-wound dressing 302 includes a cylindrical, shell bladder 304 formed from an impermeable, elastic material. The cylindrical, shell bladder 304 is similar in form to a modeling balloon. An exterior 305 of the cylindrical, shell bladder 304 is surrounded by a first concentric member 306 that is formed from a manifolding material, such as an open-cell foam or other materials previously mentioned in connection with the first longitudinal concentric member 120. The first concentric member 306 may be surrounded by a second concentric member (not shown but analogous to second concentric member 124).

The cylindrical, shell bladder 304 is sealed at both its proximal end 308 and distal end 310 to form an interior space 312. The interior space 312 is filled with a gas, such as air, nitrogen or other inert gas. The distal end 310 of the cylindrical, shell bladder 304 is folded back into the cylindrical, shell bladder 304 to form a portion 314 that is operable to unfurl when subjected to reduced pressure. FIG. 10A shows the cylindrical, shell bladder 304 folded into itself to create the furled state. As reduced pressure is applied, the increasing relative pressure of the gas within the cylindrical, shell bladder 304 causes the portion 314 to unfurl or expand in a longitudinally outward direction. Thus, as shown in FIG. 10B, a reduced pressure is applied that causes the reduced-pressure, tunnel-wound dressing 302 to expand as suggested by arrow 316 from an initial longitudinal length $L_1$ (FIG. 10A) to a length $L_2$ (FIG. 10B). The reduced-pressure, tunnel-wound dressing 302 may continue to expand until the distal end 310 unfolds completely.

The reduced-pressure, tunnel-wound dressing 302 is inserted into a tunnel wound (e.g., tunnel wound 104 of FIG. 1). The tunnel wound is covered with a sealing member (e.g., sealing member 136 in FIG. 1) to form a sealed space (e.g., sealed space 138 in FIG. 1) over the tunnel wound and the reduced-pressure, tunnel-wound dressing 302. Reduced pressure is then applied to the sealed space by a reduced-pressure conduit (e.g., reduced-pressure conduit 142 in FIG. 1). As the reduced pressure is applied, the reduced-pressure, tunnel-wound dressing 302 unfurls until the reduced-pressure, tunnel-wound dressing 302 reaches an obstacle, such as the bottom of the tunnel wound (e.g., bottom 134 in FIG. 1). In addition, an exterior 318 of the reduced-pressure, tunnel-wound dressing 302 expands to form or help form intimate contact with the tunnel margins of the tunnel wound. In other words, the reduced-pressure, tunnel-wound dressing 302 goes from an initial diameter $D_1$ to an expanded diameter $D_2$, where $D_2 > D_1$. The reduced pressure also pulls the tunnel margins towards the exterior 318. Reduced pressure may be applied to the tunnel margin of the tunnel wound with the help of the first concentric member 306 for a desired treatment time.

After treatment, the reduced pressure is eliminated and the tunnel margins retract from the reduced-pressure, tunnel-wound dressing 302 and thereby facilitate retraction of the reduced-pressure, tunnel-wound dressing 302 from the tunnel wound. The central bladder 310 is molded with a memory effect such that when the pressure is removed, the central bladder 310 retracts to an original position. The ambient pressure outside of the reduced-pressure, tunnel-wound dressing 302 urges the reduced-pressure, tunnel-wound dressing 302 back to the original position.

In yet another alternative embodiment, the reduced-pressure, tunnel-wound dressing 302 may be coupled to a fluid source that provides positive pressure into the interior space 312. The healthcare provider can insert the reduced-pressure, tunnel-wound dressing 302 and then manually inflate the reduced-pressure, tunnel-wound dressing 302 as desired using the fluid source. The fluid source may be, for example, a pressurized saline source.

Referring again to FIGS. 1-4, in one embodiment, the reduced-pressure, tunnel-wound dressing 102 may be formed with a longitudinal core member 118 and a first longitudinal concentric member 120 (but no second longitudinal concentric member 124) both made from a bioresorbable or dissolvable material. With this embodiment, the reduced-pressure, tunnel-wound dressing 102 may be left in the tunnel wound 104 until the reduced-pressure, tunnel-wound dressing 102 dissolves. In an analogous embodiment, the reduced-pressure, tunnel-wound dressing 102 is formed the same way but with a semi-rigid, inner-core member 155 of FIG. 7 added. The semi-rigid, inner-core member 155 may be removable. In such a case, the semi-rigid, inner-core member 155 is used to place the reduced-pressure, tunnel-wound dressing 102 and then removed. Reduced pressure is applied for a desired treatment time Then the reduced-pressure, tunnel-wound dressing 102 is allowed to remain in place until dissolved.

In one illustrative embodiment, the longitudinal core member 118 expands sufficiently under reduced pressure in the treatment range (e.g., −75 to −200 mm Hg) that the overall diameter of the reduced-pressure, tunnel-wound dressing 102 is greater than the diameter before reduced pressure is applied. In other words, the diameter may be such that the $D_2$ for the reduced-pressure, tunnel-wound dressing is greater than 100% of $D_1$, e.g., $D_2 = 101\% \ D_1$, $D_2 = 102\% \ D_1$, $D_2 = 103\% \ D_1$, $D_2 = 104\% \ D_1$, $D_2 = 105\% \ D_1$, $D_2 = 106\% \ D_1$, $D_2 = 110\% \ D_1$, $D_2 = 115\% \ D_1$, etc. (or any range therebetween).

The embodiments herein help the tunnel wound to not collapse under reduced pressure. The reduced-pressure, tunnel-wound dressing actively opposes such a collapse with a portion that is expanding under reduced pressure. The reduced-pressure, tunnel-wound dressings herein facilitate even, intimate contact between the tunnel margin and the dressing along its length. The reduced-pressure, tunnel-wound dressings herein are easily sized for different depths of tunnel wounds. The reduced-pressure, tunnel-wound dressings provide rigidity and flexibility to allow placement in many tunnel wounds with tortuous and intricate paths, and the expansion of the dressings will accommodate variations in the opening of the tunnel wounds along their length. The removal of reduced pressure causes an active retraction of the reduced-pressure, tunnel-wound dressing from the tunnel margins.

Although the subject matter of this specification and its advantages have been disclosed in the context of certain illustrative, non-limiting embodiments, it should be understood that various changes, substitutions, permutations, and alterations can be made without departing from the scope thereof as defined by the appended claims. It will be appreciated that any feature that is described in connection to any one embodiment may also be applicable to any other embodiment. For example, the semi-rigid, inner-core member 155 of FIG. 7 and the conduits of FIG. 8 may be added to any other embodiment herein.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of embodiments is given by way of example only and that various modifications may be made by those skilled in the art. The above specification, examples and data provide a complete description of the structure and, use of exemplary embodiments of the subject matter herein. Although various embodiments have been described above with a certain degree of particularity, or with reference to one or more individual embodiments, those skilled in the art could make numerous alterations to the disclosed embodiments without departing from the scope of the claims.

We claim:

1. A method to treat a tunnel wound or fistula, the method comprising:
   providing a dressing, wherein the dressing comprises:
      a distal end, a proximal end, and a longitudinal profile between the distal end and the proximal end, wherein a length of the dressing between the distal end and the proximal end is greater than a width of the dressing,
      a longitudinal core member formed from a closed-cell foam and configured to expand under reduced pressure, and
      a first longitudinal concentric member formed from an open-cell foam, wherein the first longitudinal concentric member is concentrically disposed on a circumference of the longitudinal core member;
   inserting the distal end of the dressing into the tunnel wound or the fistula such that the distal end is positioned proximate to a bottom of the tunnel wound or the fistula and the proximal end of the dressing is positioned proximate to an opening of the tunnel wound or the fistula, wherein a gap is formed between the dressing and an inner wall of the tunnel wound or the fistula;

delivering the reduced pressure to the dressing to expand the longitudinal core member and to cause an outer circumference of the dressing to contact the inner wall of the tunnel wound or the fistula, wherein the first longitudinal concentric member compresses upon contact with the inner wall of the tunnel wound or the fistula; and removing the reduced pressure to retract the dressing away from the inner wall of the tunnel wound or the fistula.

2. The method of claim 1, wherein the dressing further comprises a second longitudinal concentric member formed from a non-adherent material having a plurality of apertures, and wherein the second longitudinal concentric member is concentrically disposed on a circumference of the first longitudinal concentric member.

3. The method of claim 1, wherein a diameter of the longitudinal core member expands at least 10 percent and a diameter of the first longitudinal concentric member compresses at least 10 percent when the reduced pressure is applied to the dressing.

4. The method of claim 1, further comprising introducing a liquid into the dressing.

5. The method of claim 1, wherein removing the reduced pressure comprises removing the reduced pressure in two or more stages.

6. The method of claim 1, wherein the longitudinal core member and the first longitudinal concentric member comprise bioresorbable materials, and wherein the method further comprises allowing the dressing to remain in the tunnel wound until the dressing dissolves.

* * * * *